(12) United States Patent
Tokiwa

(10) Patent No.: US 7,235,398 B2
(45) Date of Patent: Jun. 26, 2007

(54) METHOD FOR DEGRADING POLYLACTIDE RESINS

(75) Inventor: Yutaka Tokiwa, 46-12, Sakuragaoka-cho, Tsuchiura-shi, Ibaraki 300-0832 (JP)

(73) Assignees: National Institute of Advanced Industrial Science and Technology, Tokyo (JP); Yutaka Tokiwa, Ibaraki (JP)

( * ) Notice: Subject to any disclaimer, the term of this patent is extended or adjusted under 35 U.S.C. 154(b) by 0 days.

(21) Appl. No.: 10/942,463

(22) Filed: Sep. 16, 2004

(65) Prior Publication Data
US 2005/0032181 A1    Feb. 10, 2005

Related U.S. Application Data

(63) Continuation of application No. 10/089,120, filed as application No. PCT/JP00/02113 on Mar. 31, 2000, now abandoned.

(30) Foreign Application Priority Data
Nov. 4, 1999    (JP) ................................. 11-313578

(51) Int. Cl.
    C02F 3/34    (2006.01)
    C02F 3/00    (2006.01)
    C12N 1/20    (2006.01)
(52) U.S. Cl. .................... 435/262; 435/252.1; 435/822
(58) Field of Classification Search ............. 435/252.1, 435/262, 822
See application file for complete search history.

(56) References Cited

U.S. PATENT DOCUMENTS

| 4,870,019 A |   | 9/1989 | Kirby et al. |             |
|-------------|---|--------|--------------|-------------|
| 5,925,556 A |   | 7/1999 | Tokiwa et al. | ........... 435/252.1 |
| 6,066,492 A | * | 5/2000 | Tokiwa et al. | ........... 435/253.5 |

FOREIGN PATENT DOCUMENTS

| JP | 09-037776 | 2/1997 |
| JP | 11-046755 | 2/1999 |
| JP | 11-127850 | 5/1999 |

OTHER PUBLICATIONS

Williams D.F. "Enzymatic hydrolysis of polylactic acid". Engineering in Medicine. 1981, vol. 10, No. 1, pp. 5-7.*

ATCC Bacteria and Bacteriophages. 19th edition. 1996, pp. 314-315.*

Nishida et al., "Microbial degradation of poly($\rho$-dioxanone) I. Isolation of degrading microorganisms and microbial decomposition in pure culture", Polymer Degradation and Stability 68:205-217 (2000), Apr. 25, 2000.

Nishida et al., "Microbial degradation of poly($\rho$-dioxanone) II. Isolation of hydrolyzates-utilizing microorganisms and utilization of poly($\rho$-dioxanone) by mixed culture" Polymer Degradation and Stability 68:271-280 (2000), Apr. 25, 2000.

Pranamuda et al., "Polylactide Degradation by an *Amycolatopsis* sp." App. Environ. Microbiol., 63(4):1637-1640 (1997).

Calmels et al., "Nuclear Localization of Bacterial *Streptoalloteichus hindustanus* Bleomycin Resistance Protein in Mammalian Cells", Mol. Pharm. 44 (6):1135-1141 (1993).

Cho et al., "Application of the ribonuclease P (RNAse P) RNA gene sequence for phylogenetic analysis of the genus *Saccharomonospora*", Int. J. System. Bacteriol. Soc. Gen. Microbiol., 48:1223-1230 (1998).

Hsieh et al., "Inhibition of Erythromycin Synthesis by Disruption of Malonyl-Coenzyme A Decarboxylase Gene *eryM* in *Saccharopolyspora erythraea*", J. Bacteriol., 176(3):714-724 (Feb. 1994).

Ikura et al., "Isolation of a microorganism capable of degrading poly-(L-lactide)", J. Gen. Appl. Microbiol., 45:247-251 (1999).

Johnson et al., "Beta Lactamases from Actinopolyspora Halophila an Extremely Halophilic Actinomycete", XP002356555, Archives of Microbiology, 143 (4):379-386 (1986) (ABSTRACT).

Piecq et al., "Cloning and nucleotide sequence of a region of the *Kibdelosporangium aridum* genome homologous to polyketide biosynthetic genes", DNA Seq., 4(4):219-229 1994).

Tomohiko et al., Four new species of-the genus *Actinokineospora: ActinokineosporaI inagensis* sp. nov., *Actinokineospora globicatena* sp. nov., *Actinokineospora terrae* sp. nov., and *Actinokineospora diospyrosa* sp. nov., Int. J. System. Bacteriol., 45(2):371-278 (1995) (ABSTRACT).

Yassin et al., Lentzea gen. nov., a new genus of the order *Actinomycetales*, Int. J. System. Bacteriol., 45(2):357-363 (1995) (ABSTRACT).

* cited by examiner

*Primary Examiner*—Vera Afremova
(74) *Attorney, Agent, or Firm*—Fish & Richardson P.C.

(57) ABSTRACT

The present invention provides novel microorganisms that directly biodegrade polylactide resins and plastics containing the same as well as a method therefor. Specifically, the present invention provides a method for degrading polylactide resins, wherein the polylactide resins are degraded by an actinomycete belonging to the genus *Saccharothrix, Streptoalloteichus, Kibdelosporangium, Lentzea, Actinokineospora, Saccharomonospora, Saccharopolyspora*, or *Actinopolyspora*.

5 Claims, No Drawings

METHOD FOR DEGRADING POLYLACTIDE RESINS

This application is a continuation of co-pending U.S. application Ser. No. 10/089,120, filed Mar. 22, 2002, now abandoned, which is a U.S. National Phase Application of International Application No. PCT/JP00/02113, filed Mar. 31, 2000, which claims priority of Japanese Patent Application No. 11-313578, filed Nov. 4, 1999. The disclosure of U.S. application Ser. No.10/089,120; International Application No. PCT/JP00/02113; and Japanese Patent Application No. 11-313578 is incorporated herein by reference in its entirety.

FIELD OF THE INVENTION

The present invention relates to a method for degrading polylactide resins through a novel biological treatment process.

BACKGROUND OF THE INVENTION

The disposal of plastic wastes is recently an issue of concern. Incineration and landfill are major methods for disposing of plastic wastes, however, incineration accelerates global warming while a decrease in the amount of land being reclaimed is a problem related with landfill disposal. Therefore, biodegrading methods are attracting attention. Polylactide resins have biodegradability and the development of various applications as next-generation plastics is in progress. In the near future, however, as with currently used plastics, a focus on the issue of wastes is strongly expected.

Polylactide resins are polymers that are hydrolyzed in a water system and are currently employed as medical and pharmaceutical materials. Since polylactide resins can be synthesized through lactic acid fermentation from regeneratable resources such as starch, they are attracting attention as a material for biodegradable plastics to replace general-purpose plastics for which environmental degradation is difficult. Polylactic resins are classified into poly-L-lactic acid, poly-D-lactic acid, poly-DL-lactic acid, and a copolymer with other polymers, depending on the type of constitutive monomer.

It is known that an enzyme accelerates hydrolysis of polylactide resins. An enzyme for degrading polylactide resins may be a hydrolase similar to protease, lipase, or esterase, although it is not yet specified. Further, until now microorganisms for directly biodegrading polylactide resins and wastes thereof and degradation method techniques using those microorganisms have been limited to the following: the actinomycetes *Amycolatopsis mediterranei* (FERM P-14921), *Actinomadura viridis* (FERM P-16247), and *Streptomyces* spp. (FERM P-15869, FERM P-15870); and the bacteria *Staphylococcus hominis* (FERM P-15867), *Staphylococcus epidermidis* (FERM P-15868), *Bacillus subtilis* (FERM P-16181), *Bacillus circullans* (FERM P-16182), and *Bacillus stearothermophilus* (FERM P-16183), and degradation using those bacteria. Thus, it can be said that investigation of techniques for actively degrading polylactide resins has not yet been sufficiently conducted.

The object of the present invention is, therefore, to provide novel microorganisms for directly biodegrading polylactide resins and plastics containing the same and a method therefor.

SUMMARY OF THE INVENTION

In order to attain the above object, we conducted concentrated studies and screening over a wide range and as a result, found, through a microbiological technique, novel actinomycetes having excellent activities for degrading polylactide resins. This has led to the completion of the present invention.

Specifically, the present invention provides a method for degrading polylactide resins in which the polylactide resins are degraded by actinomycetes belonging to the genus *Saccharothrix*, *Streptoalloteichus*, *Kibdelosporangium*, *Lentzea*, *Actinokineospora*, *Saccharomonospora*, *Saccharopolyspora*, or *Actinopolyspora*.

According to the present invention, polylactide resins are degraded by being added to a medium containing inorganic salts together with the actinomycetes belonging to the genus *Saccharothrix*, *Streptoalloteichus*, *Kibdelosporangium*, *Lentzea*, *Actinokineospora*, *Saccharomonospora*, *Saccharopolyspora*, or *Actinopolyspora*.

More specifically, in the present invention, the actinomycete belonging to the genus *Saccharothrix* is at least one bacterium selected from the group consisting of *Saccharothrix flava*, *Saccharothrix coeruleofusca*, *Saccharothrix longispora*, *Saccharothrix australiensis*, *Saccharothrix mutabilis subsp. mutabilis*, *Saccharothrix aerocolonigenes subsp. aerocolonigenes*, *Saccharothrix syringae*, *Saccharothrix coeruleoviolacea*, *Saccharothrix cryophilis*, *Saccharothrix espanaensis*, *Saccharothrix texasensis*, and *Saccharothrix waywayandensis*; the actinomycete belonging to the genus *Streptoalloteichus* is *Streptoalloteichus hindustanus*; the actinomycete belonging to the genus *Kibdelosporangium* is *Kibdelosporangium aridum*; the actinomycete belonging to the genus *Lentzea* is *Lentzea albidocapillata*; the actinomycete belonging to the genus *Actinokineospora* is *Actinokineospora riparia*; the actinomycete belonging to the genus *Saccharomonospora* is *Saccharomonospora azurea*; the actinomycete belonging to the genus *Saccharopolyspora* is *Saccharopolyspora erythraea* or *Saccharopolyspora hordei*; and the actinomycete belonging to the genus *Actinopolyspora* is *Actinopolyspora halophila* or *Actinopolyspora mortivallis*. In the present invention, a preferable culturing condition is at a pH value between 4.0 and 10.0 and a temperature between 10 and 60° C.

This specification includes part or all of the contents as disclosed in the specification of Japanese Patent Application No. 313578/1999 (Hei 11-313578), which is a priority document of the present invention.

EMBODIMENT FOR CARRYING OUT THE INVENTION

"Polylactide resins" according to the present invention refer to polymers comprised mainly of lactic acid and include a homopolymer of polylactic acid such as poly-L-lactic acid and poly-D-lactic acid, a copolymer of poly-L/D-lactic acid, and a copolymer of polylactic acid prepared by copolymerizing the above polymers with other polymers such as ε-caprolactone and glycolide, and a blended polymer made from the above polymers or from the above polymers and other polymers. A lactic acid component in the polymer (polylactide resins) is 10% by weight or more. As a method of polymerization, a method involving direct polymerization of lactic acid, a method involving ring-breakage polymerization of lactide (a cyclic dimer of lactic acid), and the like are known. A number average molecular weight of the polylactide resins applicable to the degradation method in the present invention is about 10,000 to $10^6$, preferably about 50,000 to 300,000. The present invention, however, is not limited to these only.

Examples of commercially available polylactide resins include Lacty (Shimadzu Corporation) and Lacea (Mitsui Chemicals), however, the method of the present invention is not limited to these only.

The present invention enables degradation of polylactide resins under aerobic conditions by allowing microorganisms to degrade polylactide resins.

Novel microorganisms in which we found activities for degrading polylactide resins are actinomycetes belonging to the genus *Saccharothrix, Streptoalloteichus, Kibdelosporangium, Lentzea, Actinokineospora, Saccharomonospora, Saccharopolyspora*, or *Actinopolyspora*.

Among actinomycetes belonging to the above genera, particularly preferred are *Saccharothrix flava, Saccharothrix coeruleofusca, Saccharothrix longispora, Saccharothrix australiensis, Saccharothrix mutabilis subsp. mutabilis, Saccharothrix aerocolonigenes subsp. aerocolonigenes, Saccharothrix syringae, Saccharothrix coeruleoviolacea, Saccharothrix cryophilis, Saccharothrix espanaensis, Saccharothrix texasensis, Saccharothrix waywayandensis, Streptoalloteichus hindustanus, Kibdelosporangium aridum, Lentzea albidocapillata, Actinokineospora riparia, Saccharomonospora azurea, Saccharopolyspora erythraea, Saccharopolyspora hordei, Actinopolyspora halophila*, and *Actinopolyspora mortivallis*.

Strains used in the present invention are bacteria which, for example, are stored in facilities for repositing microorganism strains such as The Institute of Physical and Chemical Research, Japan Collection of Microorganisms (2-1 Hirosawa Wako, Saitama, Japan), and one strain or a group of microorganisms containing a plurality of strains are preferably selected for use from the group consisting of: strains belonging to the genus *Saccharothrix*, i.e., *Saccharothrix flava* (JCM 3296), *Saccharothrix coeruleofusca* (JCM 3313), *Saccharothrix longispora* (JCM 3314), *Saccharothrix australiensis* (JCM 3370), *Saccharothrix mutabilis subsp. mutabilis* (JCM 3380), *Saccharothrix aerocolonigenes subsp. aerocolonigenes* (JCM 4150), *Saccharothrix syringae* (JCM 6844), *Saccharothrix coeruleoviolacea* (JCM 9110), *Saccharothrix cryophilis* (JCM 9111), *Saccharothrix espanaensis* (JCM 9112), *Saccharothrix texasensis* (JCM 9113), and *Saccharothrix waywayandensis* (JCM 9114); strains belonging to the genus *Streptoalloteichus*, i.e., *Streptoalloteichus hindustanus* (JCM 3268); strains belonging to the genus *Kibdelosporangium*, i.e., *Kibdelosporangium aridum subsp. aridum* (JCM 7912), and *Kibdelosporangium aridum subsp. largum* (JCM 9107); strains belonging to the genus *Lentzea*, i.e., *Lentzea albidocapillata* (JCM 9732); strains belonging to the genus *Actinokineospora*, i.e., *Actinokineospora riparia* (JCM 7471); strains belonging to the genus *Saccharomonospora*, i.e., *Saccharomonospora azurea* (IFO 14651); strains belonging to the genus *Saccharopolyspora*, i.e., *Saccharopolyspora erythraea* (IFO 13426) and *Saccharopolyspora hordei* (IFO 15046); and strains belonging to the genus *Actinopolyspora*, i.e., *Actinopolyspora halophila* (JCM 3278) and *Actinopolyspora mortivallis* (JCM 7550).

Each strain of the above microorganisms or a group of microorganisms containing each strain is well known in the art and may be provided for processing of polylactide resins in a liquid state together with a culture solution containing the strain grown and cultured in a basal medium which is suitable for culturing the microorganisms, for example, a medium of inorganic salts containing a nitrogen source to which 50 to 500 ppm of yeast extract has been added. If necessary, it may be provided for treatment of polylactide resins as a preparation in powder form prepared by freeze-drying a strain in accordance with a conventional method or in a solid state such as a tablet prepared by blending the powder with various vitamins and minerals and necessary nutrients, such as yeast extract, casamino acid, peptone, and the like, followed by compression.

A basal medium used in culturing in the present invention includes inorganic salts and ammonium sulfate, ammonium phosphate, and ammonium carbonate or the like is used as a nitrogen source. As inorganic salts, commonly used culture sources such as monopotassium phosphate, dipotassium phosphate, magnesium sulfate, sodium chloride, iron (I) sulfate, sodium molybdate, sodium tungstate, or manganese sulfate are used. Unlike a common bacterial medium, addition of a minor amount of yeast extract, casamino acid, peptone, malt extract or the like is sometimes effective. Octyl glucoside, a surfactant, can be used to disperse powdery polylactic acid. Surfactants such as PLYSURF (Dai-ichi Kogyo Seiyaku Co., Ltd.) sometimes inhibit degradation of polylactic acid and thus the addition thereof is not preferred. A pH value of a medium is between 4.0 and 10.0 and preferably between 5.0 and 8.0. The culturing temperature is from 10 to 47° C., preferably 10 to 40° C.

A method for biodegrading polylactide resins according to the present invention is preferably carried out by adding the previously described basal medium, polylactide resins to be processed, and the strain, the powder, tablet, or culture solution having strains incorporated therein, in a culturing tank. Alternatively, the above strains may be incorporated into active sludge or compost. From the viewpoint of degradation efficiency, most preferably, a polylactic resin is pulverized, however it may be a film. The amount of polylactide resins injected into the basal medium is preferably 0.01 to 10% by weight with respect to the basal medium. The amount of microorganisms added may be very small, however, it is preferably 0.01% by weight or more based on the polylactide resins in order that the injected amount does not affect the process time.

The time required for degradation varies depending on the composition, form, and amount of polylactide resins, the type of microorganisms used and the relative amount thereof with respect to the resin, as well as other various culturing conditions, and thus the time cannot be completely specified. Generally, polylactide resins can be degraded by being maintained for several days to several weeks or several months under the above conditions.

The present invention will be described in more detail with reference to the following examples. The present invention, however, is not limited to these examples only.

EXAMPLE 1

100 mg of polylactic resin (poly-L-lactic acid, Mn: $1.08 \times 10^5$), pulverized to 180 micron or smaller, was added as a carbon source to 100 ml of basal medium (pH 7.0) shown in Table 1 and each strain shown in Table 2 was inoculated thereto, followed by culturing at 30° C. for four weeks in a 180 rpm rotary shaking apparatus.

TABLE 1

Formulation of basal medium (in 1 liter of distilled water)

| Component | Amount incorporated |
|---|---|
| $Na_2MoO_4 \cdot 2H_2O$ | 0.5 mg |
| $Na_2WO_4 \cdot 2H_2O$ | 0.5 mg |
| $MnSO_4$ | 0.5 mg |
| $FeSO_4 \cdot 7H_2O$ | 10 mg |
| NaCl | 10 mg |
| $CaCl_2 \cdot 2H_2O$ | 20 mg |
| $(NH_4)_2SO_4$ | 1,000 mg |
| $MgSO_4 \cdot 7H_2O$ | 200 mg |
| $K_2HPO_4$ | 1,600 mg |
| $KH_2PO_4$ | 200 mg |
| Octyl glucoside | 50 mg |
| Yeast extract | 100 mg |

TABLE 2

Degradation of polylactide resins by various actinomycetes (30° C., 4 weeks, shake culturing)

| Strain | Degradation rate of polylactic acid, % |
|---|---|
| Control (strain not inoculated) | 0.2 |
| Saccharothrix flava JCM 3296 | 30.4 |
| Saccharothrix coeruleofusca JCM 3313 | 33.6 |
| Saccharothrix longispora JCM 3314 | 47.3 |
| Saccharothrix australiensis JCM 3370 | 34.2 |
| Saccharothrix mutabilis subsp. mutabilis JCM 3380 | 50.1 |
| Saccharothrix aerocolonigenes subsp. aerocolonigenes JCM 4150 | 30.1 |
| Saccharothrix syringae JCM 6844 | 32.1 |
| Saccharothrix coeruleoviolacea JCM 9110 | 25.4 |
| Saccharothrix cryophilis JCM 9111 | 9.7 |
| Saccharothrix espanaensis JCM 9112 | 28.3 |
| Saccharothrix texasensis JCM 9113 | 32.1 |
| Saccharothrix waywayandensis JCM 9114 | 51.8 |
| Streptoalloteichus hindustanus JCM 3268 | 52.1 |
| Kibdelosporangium aridum subsp. aridum JCM 7912 | 48.7 |
| Kibdelosporangium aridum subsp. largum JCM 9107 | 10.7 |
| Lentzea albidocapillata JCM 9732 | 11.3 |
| Actinokineospora riparia JCM 7471 | 36.0 |
| Saccharomonospora azurea IFO 14651 | 27.4 |
| Saccharopolyspora erythraea IFO 13426 | 13.9 |
| Saccharopolyspora hordei IFO 15046 | 26.5 |
| Actinopolyspora halophila JCM 3278 | 23.2 |
| Actinopolyspora mortivallis JCM 7550 | 21.6 |

The degradation rate of polylactide resins was calculated by assaying the change in the recovery weight of polylactide resins (measured as dry weight of residual poly-L-lactic acid through extraction with chloroform and evaporation of chloroform) after degradation of the added pulverized polylactide resins. The results thereof are as shown in Table 2. The results show that while little change occurred in the weights before and after culturing in a control without inoculation of strains, and thus the polylactide resins were not substantially degraded, in the medium to which bacteria having degradation capability were added according to the present invention, polylactide resins decreased from about 10 to 50%.

The foregoing demonstrated that the following strains were capable of degrading macromolecular polylactide resins: Saccharothrix flava (JCM 3296), Saccharothrix coeruleofusca (JCM 3313), Saccharothrix longispora (JCM 3314), Saccharothrix australiensis (JCM 3370), Saccharothrix mutabilis subsp. mutabilis (JCM 3380), Saccharothrix aerocolonigenes subsp. aerocolonigenes (JCM 4150), Saccharothrix syringae (JCM 6844), Saccharothrix coeruleoviolacea (JCM 9110), Saccharothrix cryophilis (JCM 9111), Saccharothrix espanaensis (JCM 9112), Saccharothrix texasensis (JCM 9113), Saccharothrix waywayandensis (JCM 9114), Streptoalloteichus hindustanus (JCM 3268), Kibdelosporangium aridum subsp. aridum (JCM 7912), Kibdelosporangium aridum subsp. largum (JCM 9107), Lentzea albidocapillata (JCM 9732), Actinokineospora riparia (JCM 7471), Saccharomonospora azurea (IFO 14651), Saccharopolyspora erythraea (IFO 13426), Saccharopolyspora hordei (IFO 15046), Actinopolyspora halophila (JCM 3278), and Actinopolyspora mortivallis (JCM 7550).

All publications, patents and patent applications cited herein are incorporated herein by reference in their entirety.

INDUSTRIAL APPLICABILITY

The method for degrading polylactide resins according to the present invention is a method for disposing of polylactic resin wastes which does not generate any exhaust gas, unlike the conventional incineration method, is significantly time-saving compared to the conventional landfill technology, and is a very valuable method in waste disposal. In particular, by actively degrading polylactide resins, which are biodegradable plastics, using microorganisms having degrading activities, instead of merely waiting for natural degradation in soil, an environmentally better disposal technique can be provided. Further, the use of the disposal technique according to the present invention at composting facilities enables conversion of polylactide resins into useful materials such as organic acids or compost.

What is claimed is:

1. A method for degrading polylactide resins, wherein the polylactide resins are degraded by an actinomycete: (a) belonging to the genus Saccharothrix; and (b) that is at least one bacterium of a strain selected from the group consisting of *Saccharothrix longispora* JCM 3314, *Saccharothrix mutabilis subsp. mutabilis* JCM 3380, and *Saccharothrix waywayandensis* JCM 9114.

2. The method of claim 1, wherein the polylactide resins comprise poly-L-lactic acid or a copolymer of poly-L/D-lactic acid.

3. The method of claim 1, wherein the bacterium is of the strain *Saccharothrix longispora* JCM 3314.

4. The method of claim 1, wherein the bacterium is of the strain *Saccharothrix mutabilis subsp. mutabilis* JCM 3380.

5. The method of claim 1, wherein the bacterium is of the strain *Saccharothrix waywayandensis* JCM 9114.

* * * * *